United States Patent [19]

Nabial

[11] 4,425,328

[45] Jan. 10, 1984

[54] SOLID ANTIPERSPIRANT STICK COMPOSITION

[75] Inventor: Wanda E. Nabial, Garfield, N.J.

[73] Assignee: American Cyanamid Company, Stamford, Conn.

[21] Appl. No.: 333,232

[22] Filed: Dec. 21, 1981

[51] Int. Cl.³ .................. A61K 7/34; A61K 7/36; A61K 7/38
[52] U.S. Cl. ................ 424/68; 424/DIG. 5; 424/66; 424/67
[58] Field of Search ................... 424/DIG. 5

[56] References Cited

U.S. PATENT DOCUMENTS

| | | | |
|---|---|---|---|
| 4,137,306 | 1/1979 | Rubino et al. | 424/68 |
| 4,151,272 | 4/1979 | Geary et al. | 424/Dig. 5 |
| 4,229,432 | 10/1980 | Geria | 424/DIG. 5 |
| 4,265,878 | 5/1981 | Keil | 424/DIG. 5 |
| 4,280,994 | 7/1981 | Turney | 424/DIG. 5 |

FOREIGN PATENT DOCUMENTS 24365  4/1981  European Pat. Off. ...... 424/DIG. 5

OTHER PUBLICATIONS

Drug & Cosmetic Industry, 5/1980, vol. 126, (Jan.–Jun. 1980) Ciulla.
CTFA Cosmetic Ingredient Dictionary, 2nd. edition, Estrin (editor).
NL Industries Bulletin, 8/14/1979, pp. 1 to 9.

*Primary Examiner*—Dale R. Ore
*Attorney, Agent, or Firm*—Charles J. Fickey

[57] ABSTRACT

Base compositions which are hydrophobic waxy matrixes for cosmetic preparations such as antiperspirants and deodorants containing volatile silicones as emollients, wherein the amount of silicone may be reduced by use of certain liquid polyoxypropylene-alkyl ethers as emmolients, and the efficacy astringent metal salts as antiperspirants may be enhanced by the use of a combination of stearic acid and hydroxy stearic acid.

7 Claims, No Drawings

SOLID ANTIPERSPIRANT STICK COMPOSITION

This invention relates to improvements in bases useful for cosmetic preparations in general and for antiperspirants and deodorants in particular. More specifically, the invention relates to wax-like compositions useful for antiperspirant sticks which are generally hydrophobic in nature and which contain ingredients to improve the efficacy and aesthetic properties thereof.

In general, the antiperspirant or deodorant sticks consist of a hydrophobic waxy matrix which functions as a base for an active ingredient. In the case of antiperspirant sticks, the active ingredient is an astringent, such aluminum chlorohydrate or other similarly used compounds. The waxy matrix may, of course, consist of many ingredients to provide specific desirable properties.

Effective antiperspirant stick compositions containing stearyl alcohol, a highly ethoxylated stearyl alcohol and a volatile silicone compound are disclosed by Geary et al. in U.S. Pat. No. 4,151,272. Although such compositions, which contain large amounts of volatile silicone compound, are effective, they are expensive to make. Efforts are continuing to improve both the efficacy and the aesthetic properties of antiperspirant sticks while decreasing the cost of the product.

It has been discovered that the efficacy of antiperspirant sticks, containing an active astringent suspended in a waxy matrix, is boosted if the matrix contains, in addition to stearyl alcohol, a combination of stearic acid and hydrostearic acid. It has also been discovered that the highly desirable emollient properties obtained by the use of large concentrations of a volatile silicone are achieved by the use of lower concentrations of a volatile silicone in combination with certain liquid polyoxypropylene-alkyl ethers and, optionally mineral oil in amounts described hereinbelow.

The compositions of the invention have distinct advantages over sticks containing high (>50%) concentrations of volatile silicones in being much less expensive while at the same time exhibiting equivalent aesthetic properties, for example, slip, non-oily feel, and the like. Moreover, the novel use of stearic acid/hydrosystearic acid provides antiperspirant efficacy comparable to stearyl alcoholbased sticks containing high concentrations of volatile silicones.

Aluminum chlorhydrate and aluminum-zirconium hydroxy chloride and many other active astringent compounds show good antiperspirant efficacy using recognized efficacy-testing protocols when applied as a solution to humans.

These same compounds, when incorporated into antiperspirant sticks containing stearyl alcohol, or other fatty alcohols, are coated with the hydrophobic waxy material, thereby preventing or hindering the water of perspiration from contacting the active astringent. Moreover, the liquid polyoxypropylene-alkyl ethers used in the compositions of the invention will also coat the astringent particles, unlike the silicone used in Geary et al. in U.S. Pat. No. 4,151,272, which volatilizes upon application. Thus, antiperspirant sticks containing volatile silicone and polyoxypropylene-alkyl ethers, absent the stearic acid/hydroxystearic acid of the invention, are less efficacious. While applicant does not wish to be limited by any expostulation of the mechanism of activity of the invention, it may be hypothesized that the addition of the more hydrophilic stearic acid/hydroxystearic acid combination of the invention boosts the efficacy by permitting greater access of perspiration to the active astringent material. A significant increase in efficacy is achieved.

Essentially, the compositions of the invention comprise an active astringent compound suspended in a waxy matrix system containing the emollients described hereinabove.

Among the useful astringents are aluminum chlorohydrate, aluminum chloride, aluminum sulfate, aluminum sulfocarbolate, aluminum-zirconium chlorohydrate, zinc sulfocarbolate, zinc sulfate, zirconium salts, such as zirconium chlorohydrate, combinations of aluminum chloride and aluminum-zirconium chlorohydrate, aluminum-zirconium chlorohydroglycine, and the like. Aluminum chlorohydrate is the preferred astringent, and most preferred is aluminum chlorohydrate having an average particle size of about 40–50 microns. The amount of active astringent may vary form about 15 to 35 percent by weight, preferably about 25–30 percent by weight.

The astringent material, for purposes of the present invention, is suspended in the waxy matrix using an organically reacted clay, such as dimethyl stearyl ammonium chloride treated hectorite (sold by NL Industries, for example, as Bentone 27). Other similarly treated clays may be used as the suspending agent, for example, Bentone 34 or 38. The activating agent for the suspending agent may be either propylene carbonate, ethanol, or other suitable polar solvents. In order to adequately suspend the astringent material, the clay must first be fully activated in the form of a gel. In the present invention, the clay is activated in the liquid polyoxy-propylene-alkyl ether by propylene carbonate, the ether/clay/propylene carbonate ratio being 9:3:1. This ratio appears to be critical to obtaining maximum swelling of the clay. Other suspending agents which may be used include the fumed silicas or thixotropic additives, such as trihydroxystearin. The stearalkonium treated clays are preferred.

The waxy matrix for the antiperspirant sticks comprises from about 15 to 25 percent by weight of stearyl alcohol, about 1 to 3 percent by weight of stearic acid, and about 1 to 2 percent by weight of hydroxystearic acid. Preferably, stearyl alcohol comprises about 20% and the stearic acid/hydroxystearic acid about 1% each. Greater amounts of either component tend to harden the antiperspirant stick. The waxy base has been found to be too soft if significantly less than about 15% stearyl alcohol is used. Stearyl alcohol, which is the preferred low melting waxy base for the compositions of the invention, may be replaced by other low melting $C_{14}$ to $C_{22}$ alcohols, that is, melting between about 100°–175° F., such as cetyl alcohol, myristyl alcohol, behenyl alcohol, and the like.

An emulsifier, such as polyoxyethylene (100) stearyl alcohol, may be added to improve the stick matrix and to facilitate removal of the antiperspirant during bathing. A number of other surfactants may be suitable for this purpose, for example, sorbitan fatty esters, polyethylene sorbitol lanolin derivatives, polyoxyethylene lanolin derivatives, polyoxyethylene fatty ethers, polyethylene (25) propylene glycol stearate, polyoxyethylene stearates, polyoxyethylene sorbitan fatty ethers, and the like. Preferred are highly ethoxylated fatty alcohols, that is, containing 100–200 moles of combined ethylene oxide, consisting of ethoxylated stearyl or cetyl alcohols or stearates. The emulsifier is present about 1–3%.

The emollient system of the invention comprises about 15 to 28 percent by weight of a volatile silicone, about 15 to 25 percent by weight of a liquid polyoxypropylene-alkyl ether, such as polyoxypropylene (14) butyl ether, and up to 5 percent by weight of mineral oil. The latter component preferably comprises about 1 to 3 percent by weight. The silicone/polyoxypropylene-alkyl ether ratio is preferably about 1:1, with both ingredients being present in an amount of about 20% by weight.

Volatile silicones are nonstaining and non-sticky. Silicones volatile under normal conditions of use which include certain cyclic silicones, that are oligomers of dimethyl siloxane, are preferred. Examples of such cyclic silicones include the methyl tetramer 2,4,6,9-octamethylcyclotetrasiloxane, the cyclic pentamer 2,4,6,8,10-decamethylcyclopentasiloxane and the cyclic hexamer 2,4,6,8,10,12-dodecamethylcyclohexasiloxane. The pentamer is preferred.

The cyclic silicones are isolated from the hydrolysis product of dimethyldichlorosilane; see Patnode et al, *J. Am. Chem. Soc.* 68, 358 (1946).

Polyoxypropylene-alkyl ethers useful in the invention are liquid members of the products of condensation of propylene oxide with an aliphatic alcohol represented by the formula:

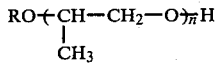

A preferred member is polyoxypropylene (14)-butyl ether.

Other emollients which can be used for practical replacement of silicone include fatty acid esters (for example, isopropyl myristate, isopropyl palmitate), branched chain fatty acid esters (for example, 2-ethylhexyl palmitate), polyoxyalkylene glycol esters (for example, polypropyleneglycol 2000-monooleate), propyleneglycol diesters of short chain dicarboxylic acids (for example, $C_8$ to $C_{10}$ dicarboxylic acids), polyoxyethylene ethers (for example, polyoxyethylene (4) lauryl ether), polyoxyethylene fatty acids, higher fatty alcohols (for example, oleyl, hexadecyl, lauryl).

It has been found by efficacy studies that the compositions of the invention show 75% more sweat reduction than similar compositions containing only stearyl alcohol as the wax component. It has also been found that the compositions of the invention are perceived to be equal in aesthetic properties to similar compositions containing 50% volatile silicone.

EXAMPLE 1

A preferred antiperspirant composition, according to the invention, has the following composition:

| | Percent by Weight |
|---|---|
| Aluminum chlorhydrate (44 microns) | 27.5 |
| Cyclic silicone pentamer | 26.34 |
| Stearic acid | 1.0 |
| Hydroxystearic acid | 1.0 |
| Stearyl alcohol | 20.0 |
| PPG (14) butyl ether | 19.20 |
| Bentone 27 | 0.5 |
| Propylene carbonate | 0.15 |
| Mineral oil | 2.0 |
| POE-100 stearyl alcohol | 1.5 |
| Color, fragrance | 0.81 |
| | 100.00 |

EXAMPLE 2

| | Percent by Weight |
|---|---|
| Aluminum zirconium chlorhydrate | 23 |
| Cyclic silicone pentamer | 22.3 |
| Stearic acid | 2 |
| Hydroxystearic acid | 1.3 |
| Cetyl alcohol | 24 |
| 2-ethylhexyl palmitate | 22 |
| Bentone 34 | 1.3 |
| Ethanol | 0.3 |
| POE-100 stearyl alcohol | 3 |
| Color, fragrance | 0.8 |
| | 100.00 |

EXAMPLE 3

| | Percent by Weight |
|---|---|
| Aluminum chlorhydrate (44 microns) | 29 |
| Cyclic silicone tetramer | 20 |
| Stearic acid | 1.5 |
| Hydroxystearic acid | 1.0 |
| Myristyl alcohol | 20 |
| Polypropylene glycol 2000-monooleate | 23 |
| Fumed silica | 1.1 |
| Propylene carbonate | 0.3 |
| Mineral oil | 2.0 |
| Polyoxyethylene (25) propylene glycol stearate | 1.3 |
| Color, fragrance | 0.8 |
| | 100.00 |

I claim:

1. A solid antiperspirant stick composition consisting essentially of:
   A. about 15 to 35 percent by weight of an astringent material suspended in
   B. a waxy matrix, comprising about 17 to 30 percent by weight of said composition and consisting essentially of:
      (1) about 15 to 25 percent by weight of a fatty alcohol,
      (2) about 1 to 3 percent by weight of stearic acid,
      (3) about 1 to 2 percent by weight of hydroxystearic acid; said matrix containing
   C. an emollient, comprising about 30 to 55 percent by weight of said composition and consisting essentially of:
      (1) about 15 to 28 percent by weight of a volatile silicone compound,
      (2) about 15 to 25 percent by weight of a liquid polyoxypropylene-alkyl ether,
      (3) about 0 to 5 percent by weight of mineral oil; said astringent material being suspended in said waxy matrix using a suspending agent.

2. The composition of claim 1 wherein said suspending agent consists of a dimethylstearylammonium chloride treated hectorite clay and propylene carbonate, wherein the weight ratio of clay to propylene carbonate is about 3 to 1.

3. The composition of claim 1 wherein said astringent material is an astringent metal salt.

4. The composition of claim 3 wherein said astringent metal salt is aluminum chlorhydrate.

5. The composition of claim 1 wherein said fatty alcohol contains from 14 to 22 carbon atoms in the alkyl chain.

6. The composition of claim 5 wherein said fatty alcohol is stearyl alcohol.

7. The composition of claim 1 containing in addition fatty acid esters.

* * * * *